US009053535B2

(12) United States Patent
Florent et al.

(10) Patent No.: US 9,053,535 B2
(45) Date of Patent: Jun. 9, 2015

(54) ADAPTIVE ROADMAPPING

(75) Inventors: Raoul Florent, Eindhoven (NL); Vincent Auvray, Eindhoven (NL); Michael Grass, Eindhoven (NL); Dirk Schaefer, Eindhoven (NL); Gert Schoonenberg, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 117 days.

(21) Appl. No.: 13/810,680

(22) PCT Filed: Jul. 15, 2011

(86) PCT No.: PCT/IB2011/053168
§ 371 (c)(1),
(2), (4) Date: Jan. 17, 2013

(87) PCT Pub. No.: WO2012/011035
PCT Pub. Date: Jan. 26, 2012

(65) Prior Publication Data
US 2013/0322724 A1    Dec. 5, 2013

(30) Foreign Application Priority Data

Jul. 19, 2010  (EP) .................................. 10305792

(51) Int. Cl.
*G06K 9/00* (2006.01)
*G06T 7/00* (2006.01)
(Continued)

(52) U.S. Cl.
CPC ................. *G06T 7/0012* (2013.01); *A61B 6/12* (2013.01); *A61B 6/463* (2013.01); *A61B 6/487* (2013.01);
(Continued)

(58) Field of Classification Search
None
See application file for complete search history.

(56) References Cited

U.S. PATENT DOCUMENTS

| 4,878,115 A | 10/1989 | Elion |
| 5,274,551 A | 12/1993 | Corby, Jr. |

(Continued)

FOREIGN PATENT DOCUMENTS

| DE | 102005059804 | 7/2007 |
| EP | 2160978 | 3/2010 |

(Continued)

OTHER PUBLICATIONS

Langs, "Building and Registering Parameterized 3D Models of Vessel Trees for Visualization During Intervention", Proceedings of the 17th International Conerence on Pattern Recognition, 2004, 4 Page Document.

(Continued)

*Primary Examiner* — Bhavesh Mehta
*Assistant Examiner* — Feng Niu

(57) ABSTRACT

An adaptive roadmapping device and method for examination of an object include providing pre-navigation image data representing part of the object being a vascular structure including an element of interest and having a tree-like structure with a plurality of sub-trees; generating a vessel representation based on the pre-navigation image data; acquiring live image data of the object; determining spatial relation of the pre-navigation image data and the live image data; analyzing the live image data by identifying and localizing the element in the live image data; determining a sub-tree in which the element is positioned, where the determining is based on the localization of the element and on the spatial relation; selecting a portion of the vascular structure based on the determined sub-tree; generating a combination of the live image data and an image of the selected portion of the vascular structure; and displaying the combination as a tailored roadmap.

12 Claims, 11 Drawing Sheets

(51) Int. Cl.
*A61B 6/12* (2006.01)
*A61B 6/00* (2006.01)
*A61B 19/00* (2006.01)
*G06T 19/00* (2011.01)

(52) U.S. Cl.
CPC ............... *A61B 6/504* (2013.01); *A61B 6/5235* (2013.01); *A61B 19/5225* (2013.01); *A61B 2019/5242* (2013.01); *A61B 2019/5289* (2013.01); *A61B 2019/5291* (2013.01); *G06T 7/0026* (2013.01); *G06T 2207/10121* (2013.01); *G06T 2207/30101* (2013.01); *G06T 19/00* (2013.01)

(56) References Cited

U.S. PATENT DOCUMENTS

| | | | | |
|---|---|---|---|---|
| 5,734,739 | A * | 3/1998 | Sheehan et al. | 382/128 |
| 6,389,104 | B1 * | 5/2002 | Bani-Hashemi et al. | 378/98.12 |
| 6,711,433 | B1 * | 3/2004 | Geiger et al. | 600/431 |
| 7,760,926 | B2 * | 7/2010 | Boese et al. | 382/131 |
| 8,073,221 | B2 * | 12/2011 | Kukuk et al. | 382/128 |
| 8,554,308 | B2 * | 10/2013 | Florent et al. | 600/427 |
| 8,718,349 | B2 * | 5/2014 | Florent et al. | 382/132 |
| 2006/0036167 | A1 | 2/2006 | Shina | |
| 2007/0173861 | A1 * | 7/2007 | Strommer et al. | 606/108 |
| 2008/0205722 | A1 | 8/2008 | Schaefer et al. | |
| 2008/0219536 | A1 | 9/2008 | Liao et al. | |
| 2008/0275467 | A1 | 11/2008 | Liao et al. | |
| 2009/0105579 | A1 * | 4/2009 | Garibaldi | 600/409 |
| 2009/0148009 | A1 | 6/2009 | Mielekamp et al. | |
| 2010/0049038 | A1 | 2/2010 | Florent et al. | |
| 2010/0145193 | A1 * | 6/2010 | Florent et al. | 600/427 |
| 2011/0037761 | A1 * | 2/2011 | Mistretta et al. | 345/419 |
| 2013/0116551 | A1 * | 5/2013 | Florent et al. | 600/424 |
| 2013/0336558 | A1 * | 12/2013 | Manzke et al. | 382/128 |
| 2014/0023250 | A1 * | 1/2014 | Cathier et al. | 382/128 |

FOREIGN PATENT DOCUMENTS

| | | | |
|---|---|---|---|
| WO | WO2008104921 | 9/2008 | |
| WO | WO2010041201 | 4/2010 | |
| WO | WO 2010067300 A1 * | 6/2010 | ............... A61B 6/00 |

OTHER PUBLICATIONS

Bredno et al, "Algorithmic Solutions for Live Device-to-Vessel Match," Proceedings of SPIE, vol. 5370, pp. 1486-1497.

Turski et al, "Digital Subtraction Angiography 'Road Map'", AJR vol. 139, Dec. 1982, pp. 1233-1234.

Soderman et al, "3D Roadmap in Neuroangiography: Technique and Clinical Interest", Neuroradiology, vol. 47, 2005, pp. 735-740.

Ostermeier, "2D Coronary Roadmap Overlaid on 2D Fluoroscopic Image", Siemens AG, 2010, pp. 1-6.

Saybasili et al, "Interventional MRI Using Multiple 3D Angiography Roadmaps with Real-Time Imaging", J Magn Reson Imaging, vol. 31, No. 4, 2010, pp. 1015-1019.

Hansis et al, "Four-Dimensional Cardiac Reconstruction from Rotational X-Ray Sequences—First Results for 4D Coronary Angiography", Proceedings of SPIE, vol. 7258, Medical Imaging, 2009, pp. 1-11.

* cited by examiner

ADAPTIVE ROADMAPPING

FIELD OF THE INVENTION

The present invention relates to a device and a method for adaptive roadmapping for examination of an object of interest as well as to a medical imaging system for examination of an object of interest, a computer program element, and a computer readable medium.

BACKGROUND OF THE INVENTION

Medical navigation systems are known to provide navigation information, for example to a cardiologist, a physician or other clinical stuff, to provide the user with information about an object of interest, for example a patient. Such navigation information is in particular needed during catheter interventional procedures, such as a PTCA (Percutaneous Transluminal Coronary Angioplasty), for example to treat cardiac stenoses. In WO 2008/104921, cardiac roadmapping is performed on the basis of at least one of a global correlation determination of a first image sequence of the object of interest and a second image sequence of the object of interest and a correlation determination of a first image of the object of interest and a second image of the object of interest on the basis of an identification of a first object and a second object and a first image and a second image. As a result, a 2D live image is combined with a 2D roadmap as navigating information. However, because vessel structures, in particular cardiovascular structures, are often complex, and because usually seen in projection in a 2D plane, the roadmap can be rather complex and thus the roadmap can often be perceived as complex to interpret.

SUMMARY OF THE INVENTION

Thus, there may be a need to improve the provision of information to the user as navigation information.

In the present invention, this is solved by the subject-matter of the independent claims, wherein further embodiments are incorporated in the dependent claims.

It should be noted that the following described aspects of the invention apply also for the device for adaptive roadmapping, the medical imaging system for examination of an object of interest, the method for adaptive roadmapping for examination of an object of interest, the computer program element, and the computer readable medium.

According to an exemplary embodiment of the invention, a method for adaptive roadmapping for examination of an object of interest comprises the following steps:

a) providing pre-navigation image data that represents at least a part of a vascular structure comprising a tree-like structure with a plurality of sub-trees;

b) generating a vessel representation on the basis of the pre-navigation image data;

c) acquiring live image data of the object, which object comprises the vascular structure, wherein the vascular structure contains an element of interest;

d) determining spatial relation of the pre-navigation image data and the live image data;

e) analyzing the live image data by identifying and localizing the element in the live image data;

f) determining a sub-tree in which the element is positioned, wherein the determining is based on the localization of the element and on the spatial relation, and selecting a portion of the vascular structure based on the determined sub-tree;

g) generating a combination of the live image data and an image of the selected portion of the vascular structure; and h) displaying the combination as a tailored roadmap.

According to a further exemplary embodiment, the non-selected branch portions are pruned off and the vascular structure is displayed with the selected portion only.

According to another exemplary embodiment, the non-selected vascular structure is attenuated in relation to the distance to the element, wherein the distance relates to a connecting path inside the vessel structure.

According to one aspect of the invention, the term "element" may relate to a certain physical object inside a vascular structure, for example an interventional tool. According to a further aspect, the element may relate to an interventional device, such as an endo prosthesis, like a stent, flow diverter, coil, etc., or a prosthesis, like a wire, catheter, marker, balloon etc., or an endo-vascular imaging device such as and ICE, and OCT or an IVUS probe, etc.

According to another aspect of the invention, the term "element" may relate to a physically detectable feature inside the vascular structure, such as a landmark, bone structure, calcification structure or any implanted device.

According to a further exemplary embodiment, step e) is repeated generating temporal information in case the positioning in step f) leads to a predetermined degree of ambiguity, and the temporal information is applied for determining the sub-tree in step f).

According to a further exemplary embodiment of the invention, a device for adaptive roadmapping for examination of an object of interest is provided, comprising a processing unit, an interface unit, and a display.

The interface unit is adapted to provide pre-navigation image data that represents at least a part of a vascular structure comprising a tree-like structure with a plurality of sub-trees. The interface unit is further adapted to provide live image data of the object, which object comprises the vascular structure, wherein the vascular structure contains the element of interest.

The processing unit is adapted to generate a vessel representation on the basis of the pre-navigation image data, and to determine spatial relation of the pre-navigation image data and live image data. The processing unit is further adapted to analyze the live image data by identifying and localizing an element in the live image data. The processing unit is further adapted to determine a sub-tree in which the element is positioned, wherein the determining is based on the localization of the element and on the spatial relation, and to select a portion of the vascular structure based on the determined sub-tree. The processing unit is further adapted to generate a combination of the live image data and an image of the selected portion of the vascular structure.

The display is adapted to display the combination as a tailored roadmap.

According to a further exemplary embodiment of the invention, a medical imaging system for examination of an object of interest is provided, comprising a device according to the above mentioned exemplary embodiment and X-ray image acquisition means. The X-ray image acquisition means are adapted to acquire the live image data of the object, which object comprises the vascular structure, wherein the vascular structure contains the element of interest.

These and other aspects of the present invention will become apparent from and elucidated with reference to exemplary embodiments described hereinafter.

BRIEF DESCRIPTION OF THE DRAWINGS

Exemplary embodiments of the invention will be described in the following with reference to the following drawings.

DETAILED DESCRIPTION OF EXEMPLARY EMBODIMENTS

Figure 1:
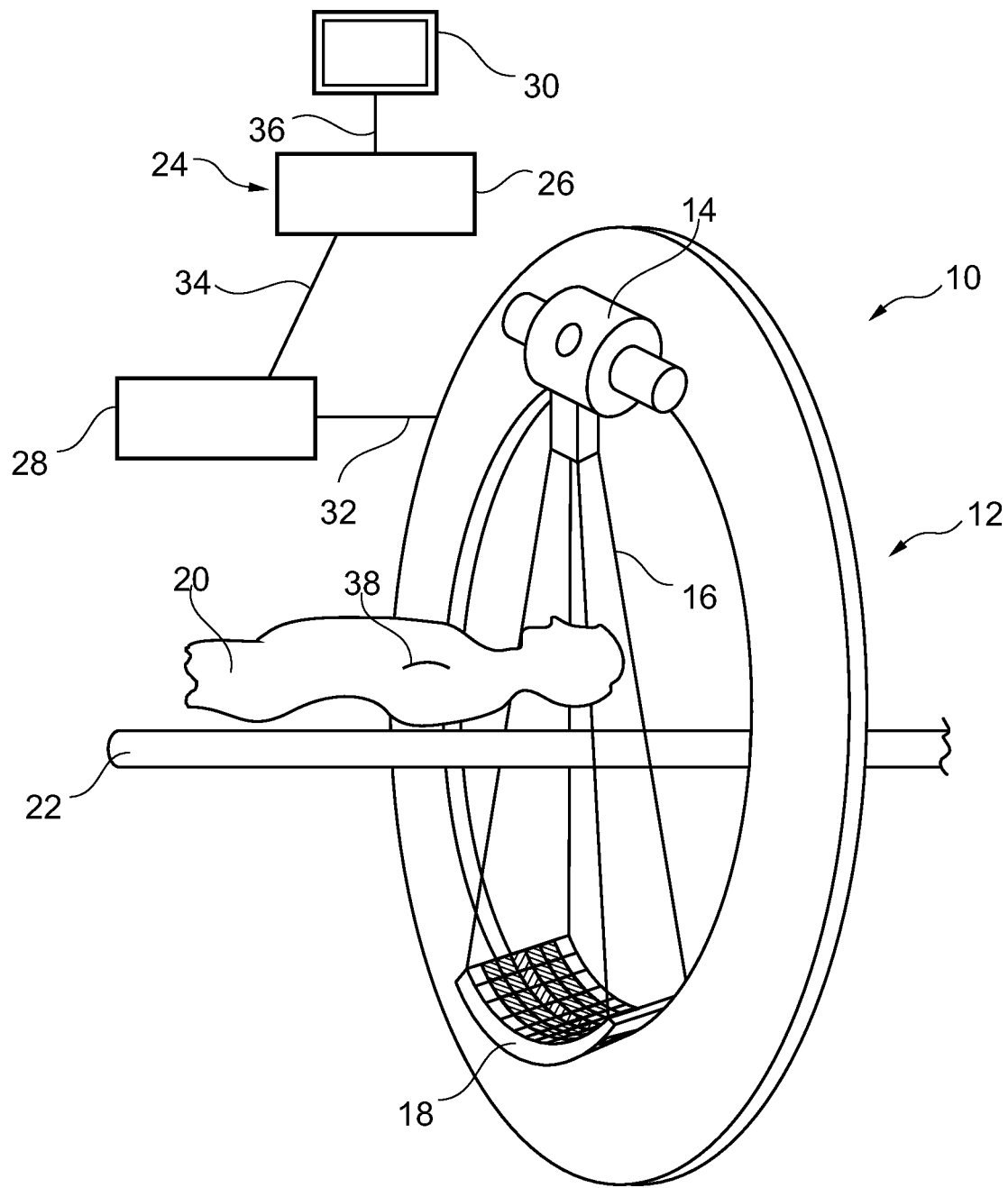
FIG. 1 illustrates an X-ray image acquisition means with a device for adaptive roadmapping according to an exemplary embodiment of the invention.

FIG. 1 schematically shows a medical image system 10 for the use, for example, in a catheterization laboratory. The medical image system 10 for examination of an object of interest comprises X-ray image acquisition means 12. The X-ray image acquisition means 12 are provided with a source of X-ray radiation 14 to generate X-ray radiation, indicated by an X-ray beam 16. Further, an X-ray image detection module 18 is located opposite the source of X-ray radiation 14 such that, for example, during a radiation procedure, an object, for example a patient 20, can be located between the X-ray source 14 and the detection module 18. Further, a table 22 is provided to receive the object to be examined.

Further, the medical imaging system 15 comprises a device 24 for adaptive roadmapping for examination of an object of interest. The device 24 comprises a processing unit 26, an interface unit 28, and a display 30.

The interface unit 28 is adapted to provide pre-navigation image data that represents at least a part of a vascular structure comprising a tree-like structure with a plurality of sub-trees. The interface unit 28 is further adapted to provide live image data of the object, which object comprises the vascular structure, wherein the vascular structure contains an element of interest, which is indicated with reference number 38.

The processing unit 26 is adapted to generate a vessel representation on the basis of the pre-navigation image data. The processing unit 26 is further adapted to determine spatial relation of the pre-navigation image data and live image data. Further, the processing unit 26 is adapted to analyze the live image data by identifying and localizing the element 38 in the live image data. The processing unit 26 is also adapted to determine a sub-tree in which the element 38 is positioned, wherein the determining is based on the localization of the element and on the spatial relation, and to select a portion of the vascular structure based on the determined sub-tree. The processing unit 26 is also adapted to generate a combination of the live image data and an image of the selected portion of the vascular structure.

According to an aspect of the invention, the element 38 may relate to a certain physical object inside a vascular structure, for example an interventional tool. According to a further aspect, the element may relate to an interventional device, such as an endo prosthesis, like a stent, flow diverter, coil, etc., or a prosthesis, like a wire, catheter, marker, balloon etc., or an endo-vascular imaging device such as and ICE, and OCT or an IVUS probe, etc.

According to another aspect of the invention, the element 38 may relate to a physically detectable feature inside the vascular structure, such as a landmark, bone structure, calcification structure or any implanted device.

The display 30 is adapted to display the combination as a tailored roadmap.

The acquisition means 12 may be adapted to acquire pre-navigation image data. The acquired pre-navigation image data is provided to the interface unit 28 which is indicated by a first connecting line 32.

Further, the acquisition means 12 are adapted to acquire the live image data of the object, which object comprises the vascular structure, wherein the vascular structure contains the element of interest. The acquired live image data is then provided to the interface unit 28 which is indicated by the first connecting line 32. The interface unit 28 provides the live image data to the processing unit which is indicated by a second connecting line 34. The generated combination is provided by the processing unit 28 to the display 30 which is indicated by a third connecting line 36. Of course, the data connections of the above mentioned units and means can also be realized with a wireless connection.

It is noted that the example shown is a so-called O-arm CT image acquisition device. Of course, the invention also relates to other types of X-ray image acquisition means, such as a C-type X-ray image acquisition device with a C-arm instead of a circular gentry, as shown in FIG. 1.

The procedure according to the invention is described in more detail below. As mentioned above, the present invention is to be used, for example, by an imaging system for PTCA in catheter laboratories, for example to treat cardiac stenoses. Of course, the present invention is also to be used for other examination or analysis procedures in which imaging data to be shown as a roadmap is complex and thus a tailored roadmap leads to enhancement with respect to the reception of provided information on the side of the user.

As mentioned above, a background of the invention is vessel roadmapping. Vessel roadmapping consists in combining a vessel representation, i.e. the roadmap, computed from pre-navigation image data to real time images used for intra-vessel device steering and positioning and where the vessels are otherwise non-visible or badly visible. Typically, this occurs in X-ray interventional situations, for example, where the vessels are only visible through contrast agent injections. Those contrast built images are produced before the actual device steering and are called angiograms. They are used for analyzing and diagnosing the situation, in the margin of the invention or during the intervention. With the roadmapping technique, the contrast filled vessels are somehow translated into a representation that can be combined to real time fluoroscopic images that are used for device navigation and positioning.

According to another aspect, vessel roadmapping can also typically be achieved by providing pre-navigation acquired with other techniques that to not require contrast agent injections. As a result, the vessel structure acquired before the actual examination, are combined with real time fluoroscopic images in order to produce roadmaps.

In 2D roadmapping, the vessels may come directly from a 2D angiogram and are overlaid to the fluoroscopy images. This can also be referred to as trace-subtract or subtract fluoroscopy.

Roadmapping techniques are mainly used on pseudo static conditions where the angiogram and fluoroscopy images correspond to mainly static vessel structures.

According to the invention, also 3D originated 2D roadmapping (referred to as 3D roadmapping) is provided consisting in building a 2D vessel representation to be overlaid on the 2D fluoroscopy images from 3D data, for instance coming from a C-arm CT approach. One of the advantages of the 3D approach is that whichever the system geometry parameters used at fluoroscopy time, one can always re-compute a relevant 2D roadmap from the 3D data projected under the right geometry, for example under the right viewing angle. Another advantage is that the vessels can be more easily identified in 3D data, so that a refined segmented or modelled view of the vessels can be used as a roadmap source as opposed to a low level iconic representation in 2D originated roadmapping.

However, a certain dose of registration might be needed to correctly align the roadmap to the real time images. Several methods can be involved, such as table panning correction, pixel shift, breathing correction, cardiac motion correction, etc.

As stated above, in general, roadmapping is a great technique that strongly improves device guidance, positioning, implantation, etc. Roadmapping provides object information of a current situation with reference to the vascular structure. However, because vascular structure, in particular cardiac or, even more so, neuro vascular structures, are often complex, the total roadmap might be rather complex and contain many distinct vessel branches. In addition, because the roadmap is projected into a 2D space, or simply originates from a 2D space, the vessels that the roadmap contains, which are inherently 3D structures, are usually strongly overlapping each other. Thus, the roadmap can often be perceived as rather cluttered and complex to interpret.

According to the invention, it is possible to automatically and dynamically identify and localize the involved element, such as an intervention device, and based on this information to compute and overlay a tailored roadmap where all the vessels that are away from the element current action range are simply pruned off or attenuated, for example. The roadmap according to the invention can also be referred to as a simplified roadmap. Basically, only the vessels and immediate branches where the device or the element is found or where it is likely to be steered or positioned to, are kept in the roadmap computing and displaying process. This means that the roadmap content is evolving as the intervention progresses. For instance, as the guide wire progresses through a vessel tree, the amount and nature of the visualized overlay vessels evolve following the vasculature context encountered around the wire tip, for example.

The resulting roadmap according to the invention is much easier to interpret and is also more focused on the intervention goal, making the intervention easier, less tiring, and possibly quicker.

Figure 2:
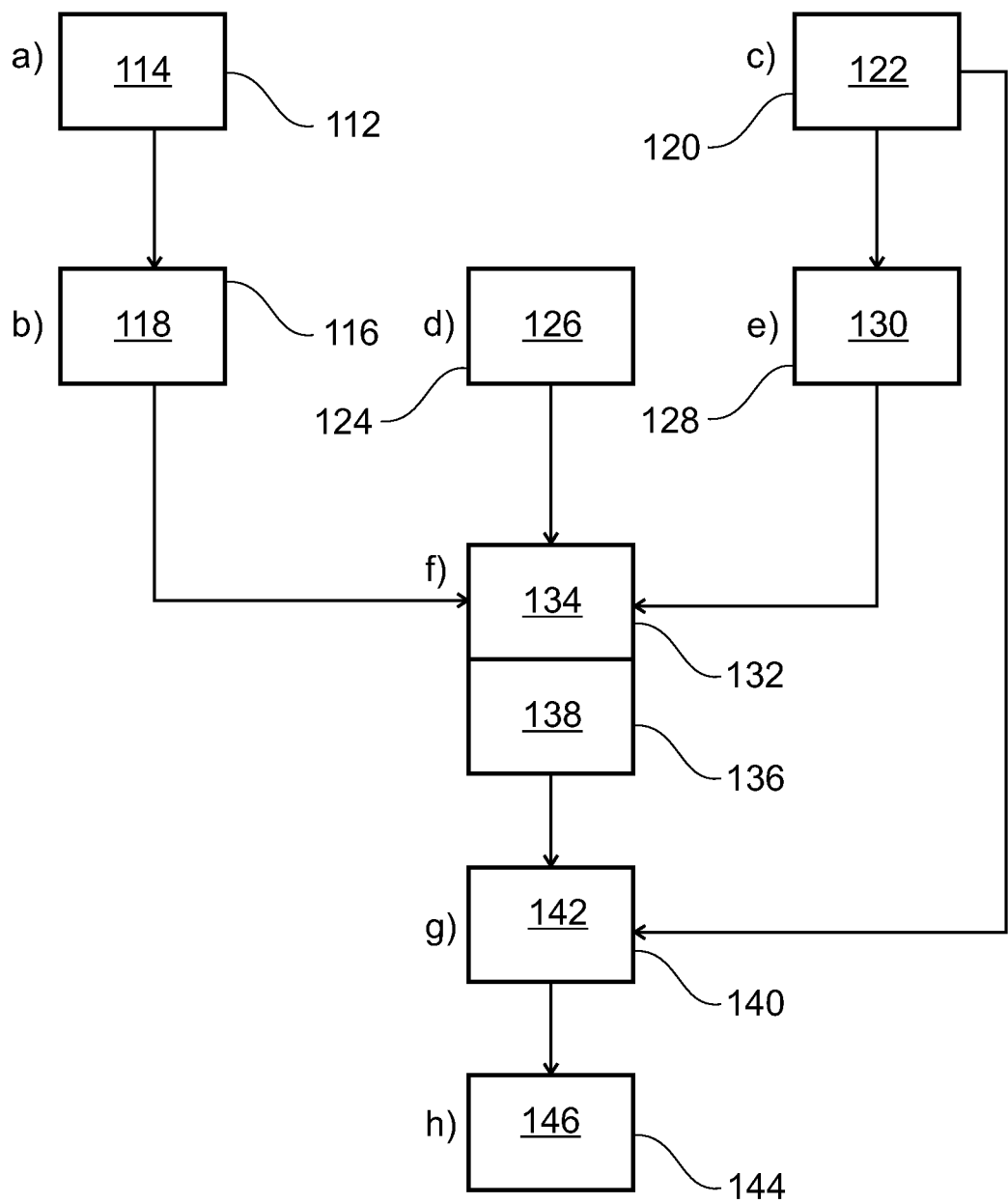
FIG. 2 schematically illustrates the basic method steps of an exemplary embodiment of the invention.

In FIG. 2, an exemplary embodiment of a method for adaptive roadmapping for examination of an object of interest is schematically described. First, in a providing step 112, pre-navigation image data 114 that represents at least a part of a vascular structure comprising a tree-like structure with a plurality of sub-trees is provided. Further, in a generating step 116, a vessel representation 118 on the basis of the pre-navigation image data 114 is generated. In an acquisition step 120, live image data 122 of the object is acquired, which object comprises the vascular structure, wherein the vascular structure contains an element of interest. In a determining step 124, spatial relation 126 of the pre-navigation image data 114 and the live image data 122 is determined. In an analysing step 128, the live image data is analyzed by identifying and localizing 130 the element in the live image data. Further, in a determining step 132, a sub-tree 134 in which the element is positioned is determined, wherein the determining is based on the localization of the element and on the spatial relation. Further, the determining step 132 also comprises selecting 136 a portion 138 of the vascular structure based on the determined sub-tree 134. Further, in a generating step 140, a combination 142 of the live image data 122 and an image of the selected portion 138 of the vascular structure is generated. In a displaying step 144, the combination 142 is displayed as a tailored roadmap 146.

In the following, the providing step 112 is also referred to as step a), the generating step 116 as step b), the acquisition step 120 as step c), the determining step 124 as step d), the analyzing step 128 as step e), the determining step 132 as step f), the generating step 140 as step g) and the displaying step 144 as step h).

It is further noted that the steps described above in FIG. 2 are only shown in an exemplary order of the steps. Of course, other orders of the steps are possible. For example, step b) is performed after one of the steps c), d), or e), but before step f). Further, the steps of e) analyzing, f) determining sub-tree, g) generating a combination and h) displaying the combination are repeated at least two times and wherein the tailored roadmap 146 is displayed as an evolving roadmap sequence.

According to a further aspect, the steps can be repeated continuously with a predetermined time rate.

According to an aspect, the step of determining the spatial relation can be fed by a) and c). According to a further aspect, the data in a) and c) can already be spatially aligned, or they might simply be spatially aligned based on the viewing angles (geometry data corresponding to a) and c)).

In the following with reference to FIGS. 3 to 9, several order and relations of the steps are described as examples.

Figure 3:
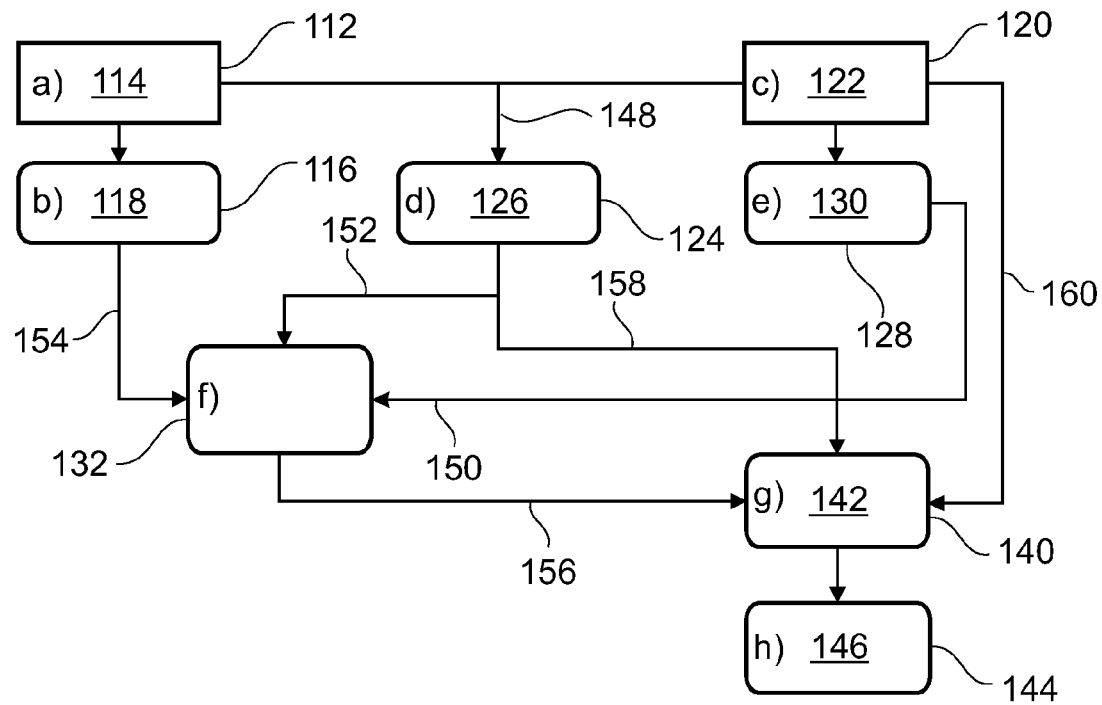
FIGS. 3 to 15 show further exemplary embodiments of method steps according to the invention.

According to FIG. 3, the pre-navigation data 114 and the live image data 122 is used for step d), i.e. determining 124 the spatial relation 126 which is indicated by an arrow 148 entering the box of step d). This is useful, for example, when one cannot entirely rely on the geometry data, that is the viewing angles, corresponding to the data a) and c). This can for instance happen in case of residual motions or of inaccuracy in the geometrical data, or even when some geometrical data are missing. In that case step d) is achieved by correlating the data a) and c) over a certain range of geometrical transforms, aiming at bringing the geometrically transformed data a) and or c) into optimal spatial alignment. The result of this operation is the set of transforms, either parametrically or explicitly coded, that achieve this optimal spatial alignment. Further, the spatial relation 126 of step d) is used for step f) where the localization data provided by step e), indicated with an arrow 150 entering the box of step f) and the vessel representation 118 provided by the generating step 116 are brought into matching based on the spatial relation 126 which is indicated by an arrow 152 coming from the box of step d) entering the box of step f), and wherein an arrow 154 coming from the box of step b) is entering step f) box, too. Further, the selected portion 138 is provided from step f) to step g) indicated by an arrow 156 entering the box of step g). Further, the spatial relation 126 is also used for step g), where the selected portion 138 and the live image data 122 are combined, for example by registering. The input of the spatial relation 126 is indicated by an arrow 158 entering the box of step g), and the entering of the live image data 122 is indicated by an arrow 160, coming from the box of step c), entering the box of step g).

It is to be noted that in FIGS. 3 to 9, steps a) and c) are indicated with square corner boxes whereas the other steps are shown with rounded corner boxes. This is illustrating that both steps a) and c) refer to data provided from a data source. Step a) refers to previously acquired image data and step c) refers to acquired live image data. The other steps with rounded corners refer to imaging processing steps.

Figure 4:
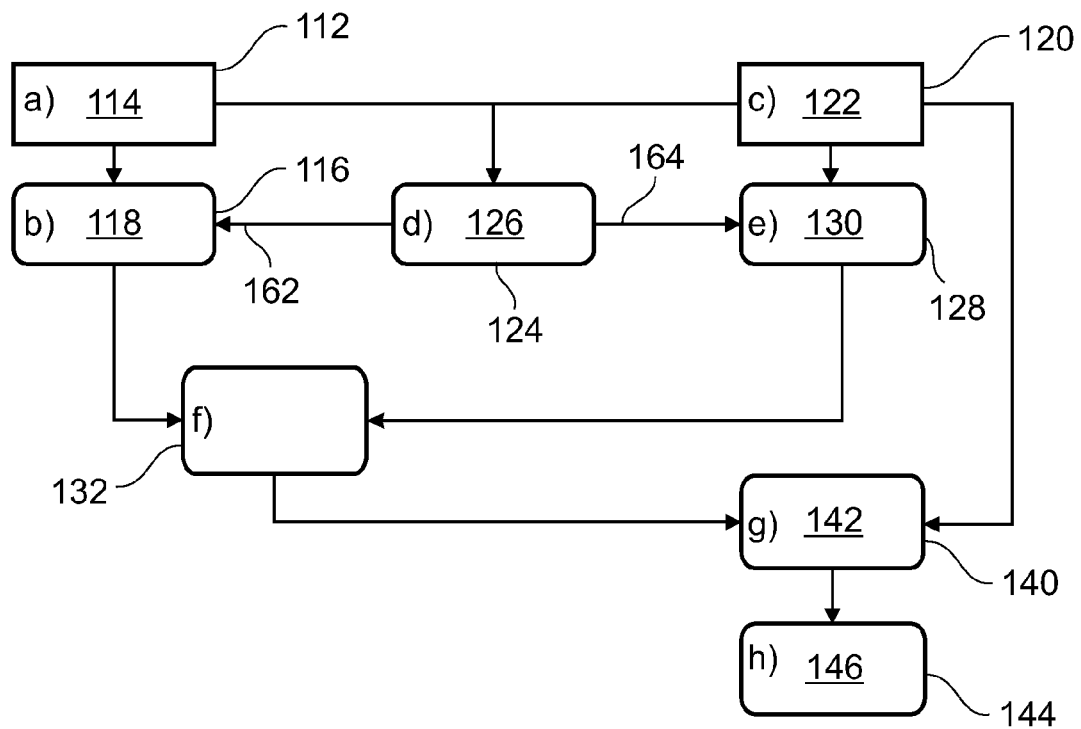

According to a further exemplary embodiment shown in FIG. 4, the spatial relation 126 of step d) is used for the generating step 116 which is indicated by an arrow 162 coming from the box of step d), entering the box of step b).

Further, the spatial relation 126 of step d) can also be used for the analysis 128 of the localization in step e), which is indicated by an arrow 164.

As shown in FIG. 4, the spatial relation 126 is thus so-to-speak comprised in the vessel representation 118 provided to step f) and also comprised in the localization data derived in step b) also provided to step f). Thus, a further input of the spatial relation directly from the box of step d) to the box of step f) is not necessary, which is indicated by missing arrows from step d) to step f) or step g).

Figure 5:
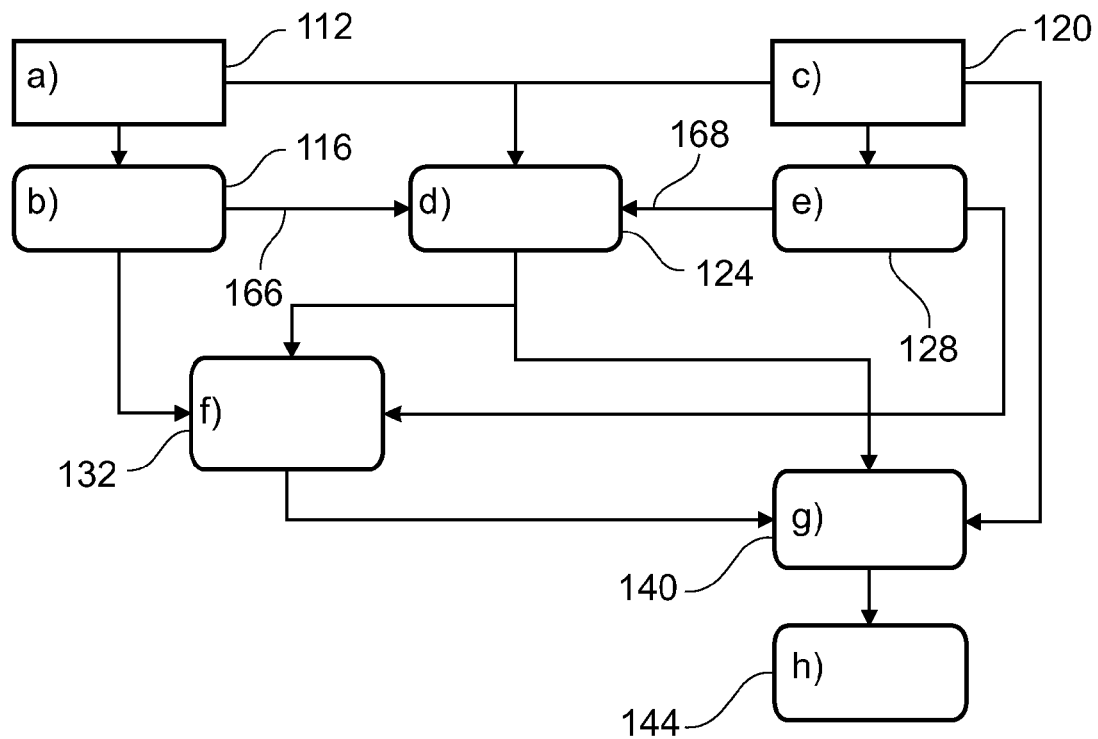

According to a further exemplary embodiment, schematically shown in FIG. 5, the determining 124 of the spatial relation 126 in step d) is performed using the pre-navigation data 118 and the live image data 122, as described above. In addition to this, the vessel representation 118 of step b) is also used for the determination 124. This is indicated by an arrow 166 coming from the box of step b), entering the box of step d). Alternatively or in addition, the localization 130 of the analyzing step 128 can also be used for the determination 124 of the spatial relation 126 in step d), which is indicated by a further arrow 168 coming from the box of step e), entering the box of step d). Thus, an enhanced or improved determination of the spatial relation is provided.

When step d) resorts to link 166 but not to link 168, this means that the determination of the spatial relationship achieved in d) exploits the fact that something resembling an intervention device in the live data should lie, after proper spatial alignment, within the vessel representation in b).

When d) resorts to link 168 but not to link 166, this means that the determination of the spatial relationship achieved in d) exploits the fact that the identified device in e) should lie, after proper spatial alignment, within something resembling a vessel in the pre-navigation data in a).

When both links 166 and 168 are used, this means that the determination of the spatial relationship achieved in d) exploits the fact that the identified device in e) should lie, after proper spatial alignment, within the vessel representation in b).

Figure 6:
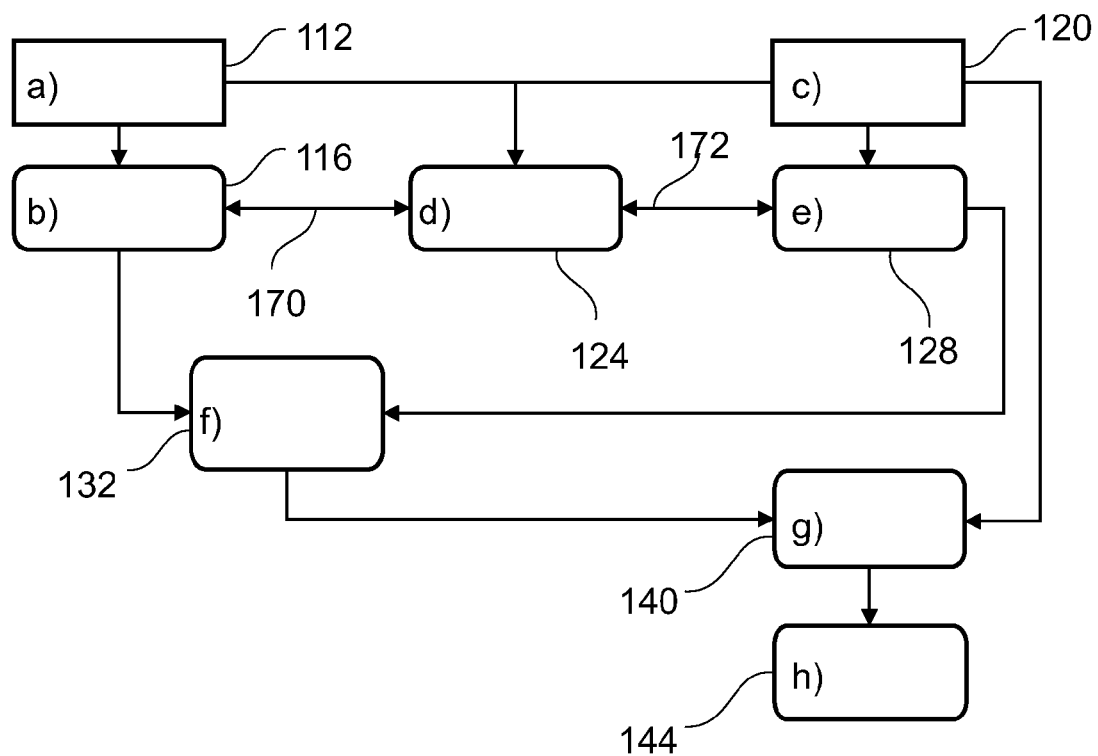

According to a further exemplary embodiment, schematically shown in FIG. 6, the determination 124 is based on the pre-navigation data 114 and live image data 122. The spatial relation 126 is provided to the vessel representation generating step b), as indicated by an arrow 170. Further, the spatial relation 126 is also provided to the analyzing step 128 which is indicated by another arrow 172. However, the vessel representation 118 and/or the localization data 130 is also provided back to the determining step 124 such that a re-determining 124 is provided, which loop-like structure is indicated by the arrows 170 and 172 having two or double arrow heads each indicating the data transfer in both directions.

According to a further aspect, the vessel representation can also be re-performed based on the spatial relation 126 determined in step d). The analysis of the localization can also be re-performed based on the spatial relation determined in step d).

Thus, the spatial relation is incorporated or so-to-speak already considered in the vessel representation 118 as well as the localization 130 such that direct input from step d) to step f) is not necessary, which is indicated by a missing arrow between these boxes.

Figure 7:
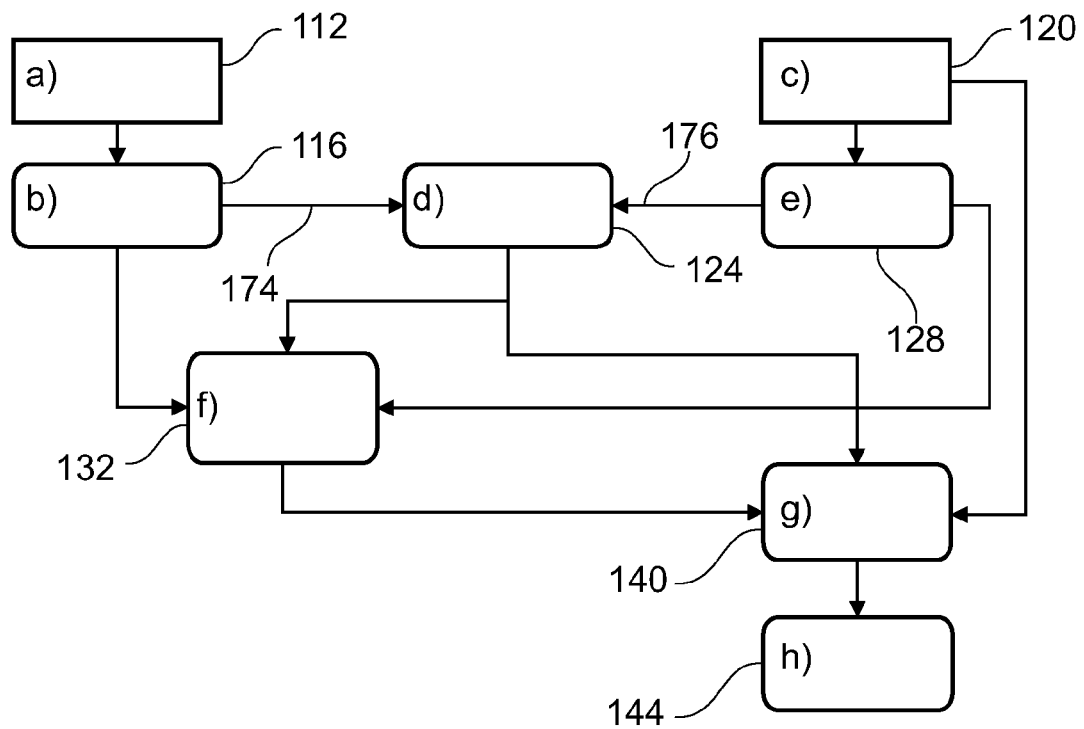

According to a further exemplary embodiment, shown in FIG. 7, the determination 124 of the spatial relation 126 in step d) is performed based on the vessel representation 118 generated in step b) and the localization 130 analyzed in step e), which is indicated by two arrows entering the determination step 124, one of which arrows 174 comes from box b) entering box d), and a second arrow 176 coming from box e) enters box d). In other words, the spatial relation determination is based directly on steps b) and e).

Figure 8:
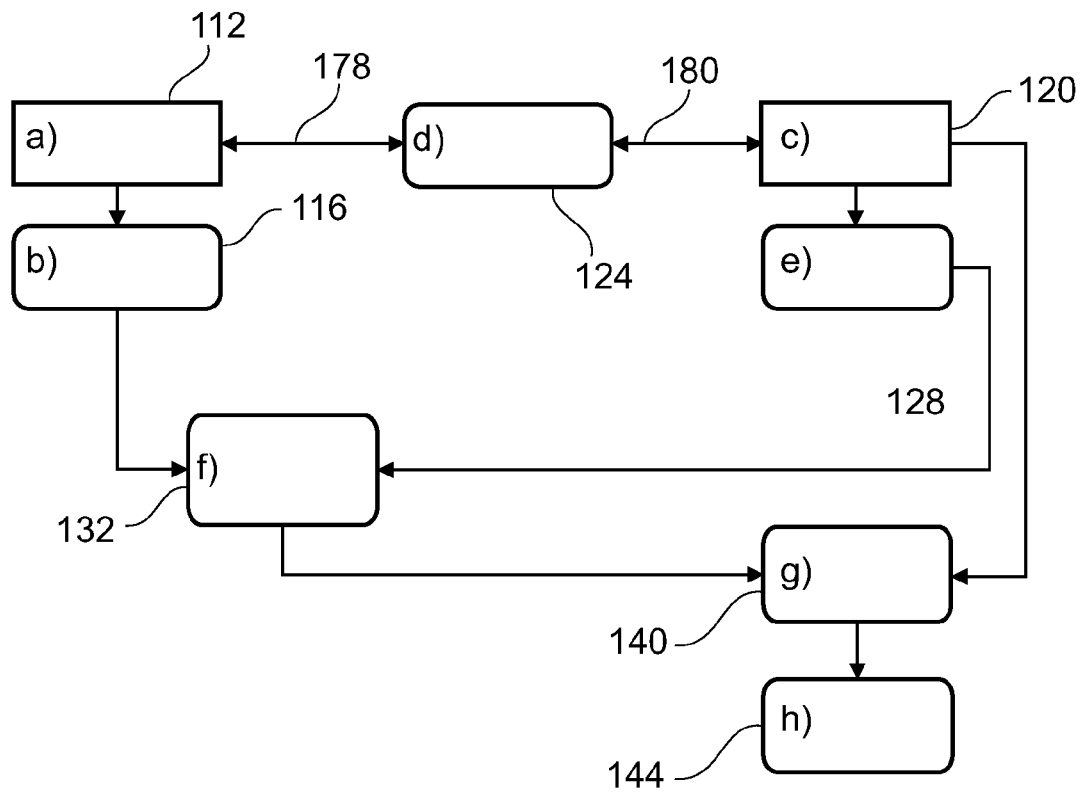

According to a further exemplary embodiment, shown in FIG. 8, the determining of the spatial relation is used for transforming one or both data of the pre-navigation data and the live image data for further processing, i.e., simply said, the pre-navigation data 114 and the live image data 122 are so-to-speak aligned to each other.

This is indicated by an arrow 178 and an arrow 180, both arrows having double arrow heads indicating the back and forth transfer of data, first entering pre-navigation data and live image data into box d), and then providing the spatial relation 126 back to the pre-navigation data box 112 and the live image data box 120. The data thus provided by step a) and step c) contains the spatial relation information determined in step d), such that the spatial relation 126 is provided to the following steps.

Thus, the box of step d) does not show any further data transfer to other boxes than the boxes of step a) and step c).

Figure 9:
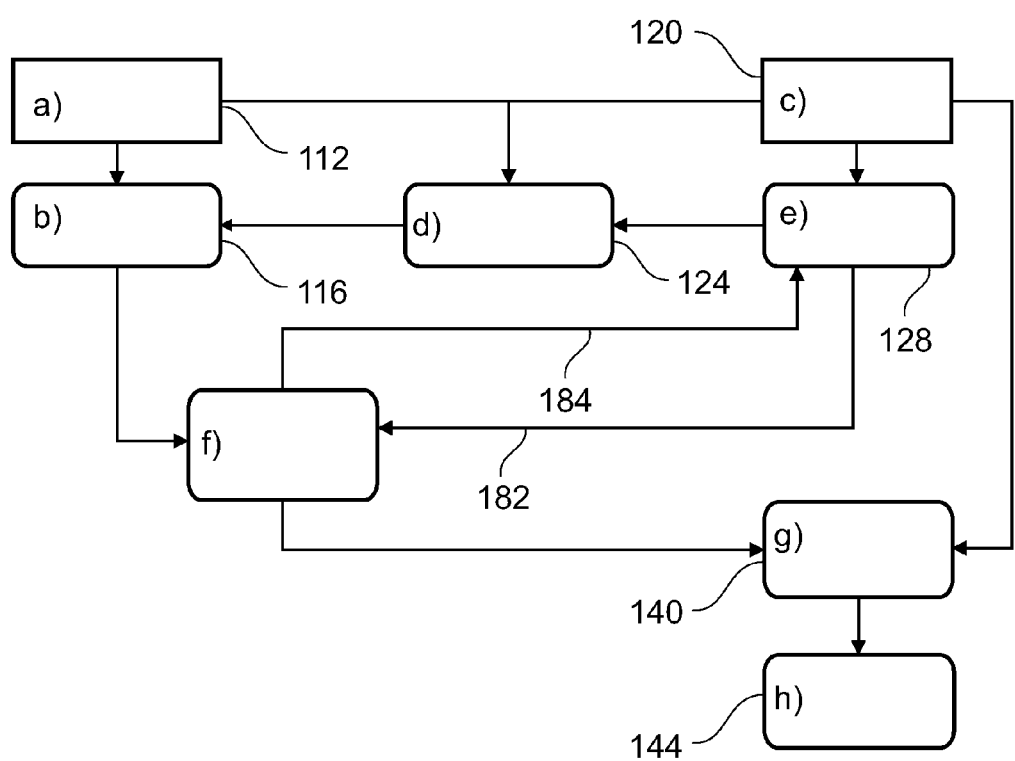

According to a further exemplary embodiment, schematically shown in FIG. 9, step e) is repeated generating temporal information in case the positioning in step f) leads to a pre-determined degree of ambiguity. The temporal information is applied for determining the sub-tree in step f). This is indicated by an arrow 182 coming from the box of step e), entering the box of step f) and another arrow 184 leaving the box f) and entering the box e).

With respect to step a), for example, the pre-navigation data is 2D image data.

According to a further aspect, the pre-navigation data is 3D image data.

According to a further aspect, the pre-navigation data is 2D+t image data or 3D+t image data.

Figure 10:
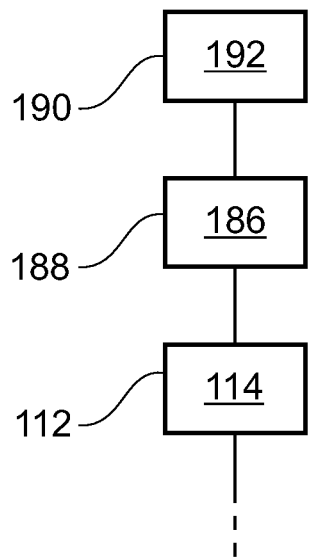

According to a further aspect, the pre-navigation data is a reconstruction 186 which is reconstructed 188 from a previously acquired 190 sequence 192 of 3D image data of the object, which is indicated in FIG. 10.

For example, the vascular structure is extracted from at least one angiographic sequence. The angiographic sequence, may, for example, be acquired in at least one angular movement.

According to a further aspect, the pre-navigation data is generated from a set of 2D projections.

According to a further aspect, the 3D image data is a 3D vessel tree achieved by a volume reconstruction based on the set of 2D projections and a vessel extraction from the reconstructed volume.

According to a further aspect, the 3D image data is provided by pre- or intra-interventional CT examination or C-arm rotation X-ray acquisition.

For example, the live image data is 2D image data. The live image data may comprise at least one 2D image.

According to a further aspect, the live image data comprises live X-ray fluoroscopy image data of the vascular structure. With reference to step b), this step may comprise generating a projection of the vascular structure on the basis of the pre-navigation data.

According to a further aspect, in 2D roadmapping, the generation comprises a grey level transformation of pixels of the pre-navigation image data.

According to a further aspect, the pre-navigation image data comprises angiogram images and step b) also comprises computing a binary mask from the angiogram images, for example through adapted filtering and thresholding.

According to a further aspect, the pre-navigation image data comprises 3D data and the representation is a full segmentation of the vascular structure present in the pre-navigation image data.

According to a further aspect, the pre-navigation image data comprises 3D data and the representation is a model of the vascular structure present in the pre-navigation image data.

With respect to step c), according to an aspect of the invention, the live image data is 2D image data. For example, the live image data comprises at least one 2D image. According to a further aspect, the 2D image data may comprise a sequence of 2D images.

According to a further aspect, the 2D images are device maps computed on a sequence of 2D images. The device map can also be referred to as an element map showing an element contained inside the vascular structure.

According to a further aspect, the live image data comprises live X-ray fluoroscopy image data of the vascular structure.

According to a further aspect, the 2D image data is acquired with acquisition parameters, such as along a viewing direction, for example.

According to a further aspect, the vascular structure is less visible in the live image data of the object than in the pre-navigation data, preferably the vascular structure is not visible in the 2D image data.

With respect to step d), according to a further aspect, step d) comprises registering the pre-navigation image data and the live image data.

According to a further aspect, the pre-navigation image data is transformed such that it matches with the live image data. Preferably, this is performed before the generating step b).

With respect to step e), according to a further aspect, the element comprises an interventional tool. According to a further aspect, the element comprises an interventional device, such as an endo prosthesis, like a stent, flow diverter, coil, etc., or a prosthesis, like a wire, catheter, marker, balloon etc., or an endo-vascular imaging device such as and ICE, and OCT or an IVUS probe, etc.

According to a further aspect, the element comprises at least two features immovably attached to the object. For example, the element comprises markers or bone structures or calcification structures of a hard vessel tree, for example.

With respect to step f), according to an exemplary embodiment of the invention, the non-selected branch portions are pruned off 194 and the vascular structure is displayed with the selected portion only. This is indicated in FIG. 11.

For example, the term "pruned off" branches comprises removed branches.

Figure 11:
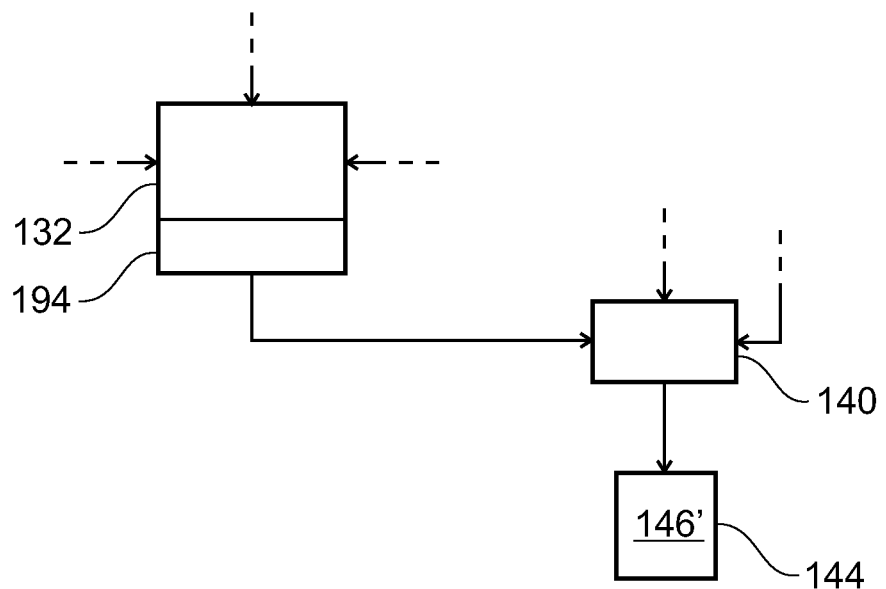

According to a further aspect, the vessel tree with pruned off branches is a segmented roadmap 146', also indicated in FIG. 11.

According to a further exemplary embodiment, in addition, the pruned off branches are shown in a valuated map (not shown).

According to a further aspect, the pruned off branches are shown in a semi-opaque manner, also not shown.

According to a further aspect, the pruned branches are shown in a different colour, which is also not shown.

Of course, according to the invention, it is also possible to combine one or any of the above mentioned embodiments.

Figure 12:
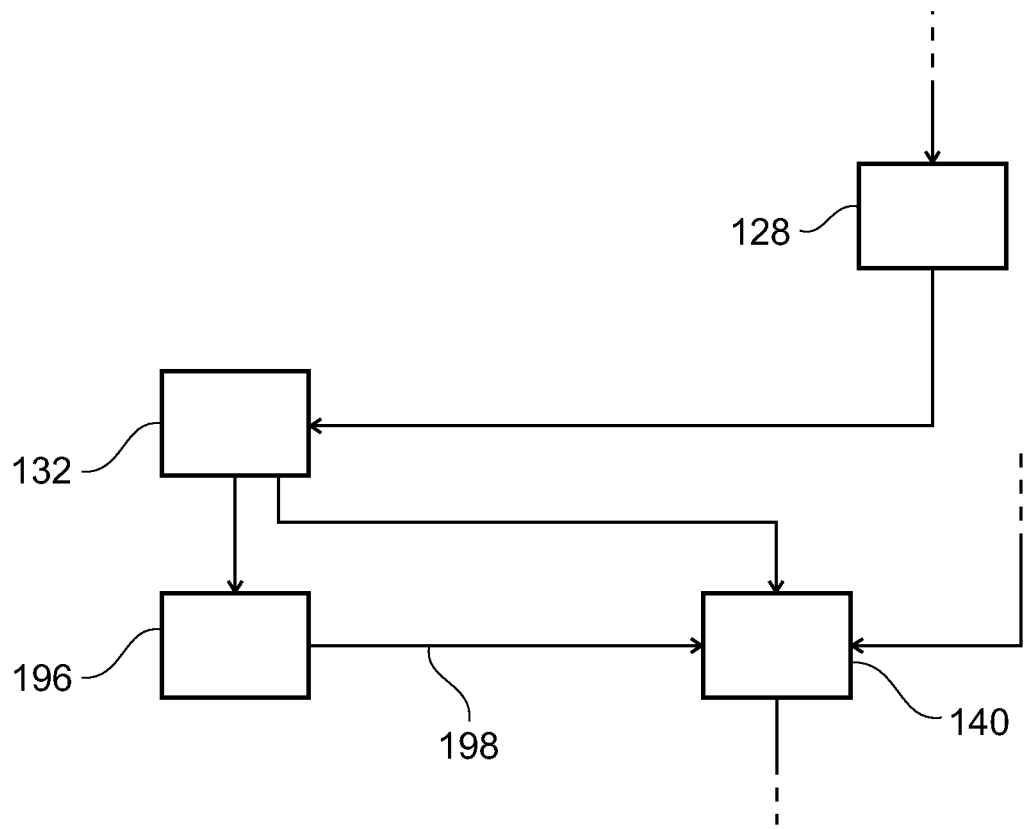

According to a further exemplary embodiment of the invention, the non-selected vascular structure is attenuated 196 in relation to the distance to the element, wherein the distance relates to a connecting path inside the tree structure (see FIG. 12). The distance is provided on the basis of the localization 130 provided in step e) entering the determination step 132 where the localization data is further forwarded to the attenuation step 196. The attenuated vascular structure is then provided to the combination step 140 which is indicated by an arrow 198 leaving the attenuation box 196, entering the box 140.

According to an aspect of the invention, the sub-trees each comprise a plurality of branches and the branch is determined in which the element is located or in which the element is likely to be steered to.

According to an aspect of the invention, the term "determined sub-tree" is related to possible, i.e. accessible, vessel portion in a forward direction, i.e. the determined sub-tree shows accessible vessels only.

According to an aspect of the invention, this might include referring not only to the anatomy but to the current intervention specificities, for example targeted aneurysm.

According to further aspect, the term "forward direction" relates to the direction from larger or main vessels to smaller secondary vessels, so-to-speak sub-vessels.

According to one aspect of the invention, the determined sub-tree is selected only.

According to a further aspect, a covered vessel path is determined based on previous localization data and the covered vessel path is indicated in the tailored roadmap.

According to a further aspect, sub-volumes adjacent to the selected sub-volume are also selected.

For example, a weighting factor is applied to the adjacent sub-volumes, for example only part volumes of the adjacent sub-volumes along the adjacent border region are selected.

According to a further aspect, the pre-navigation data comprises 3D image data that represents a volume comprising at least a part of the vascular structure, and before the volume is divided into a plurality of sub-volumes, each sub-volume containing a separate sub-tree.

According to a further aspect, the adapted roadmap can be referred to as an intelligent or enhanced roadmap tailored to the specific situation.

According to an exemplary embodiment, a plurality of sub-trees and branches are determined and the selected portion of the vascular structure is visualized in the image for the combination in step f).

According to a further exemplary embodiment, schematically shown in FIG. 9, as mentioned above, step e) is repeated 184 generating temporal information in case the positioning in step f) leads to a predetermined degree of ambiguity and wherein the temporal information is applied 182 for determining the sub-tree in step f).

According to a further aspect, the temporal information is recorded and element motion is determined on behalf of the temporal information. Based on the previously determined position inside the vessel volume, the actual vessel in which the element is positioned is identified.

For example, the identified vessel location is verified by a re-registration step (not shown).

With respect to step f), according to a further aspect, the image is a projection of the pre-navigation image data. According to a further aspect, the image is taken directly from the pre-navigation image data.

With respect to step h), according to a further aspect, alternative terms for tailored roadmap are customized roadmap, clipped roadmap, accessible roadmap, accessible path roadmap, simplified roadmap, lean roadmap, reduced roadmap, or focused roadmap just to mention some examples.

According to a further exemplary embodiment of the invention, the element located inside the vascular structure is visible in the live image data 122 and determining 124 of the spatial relation 126 is based upon the element.

Figure 13:
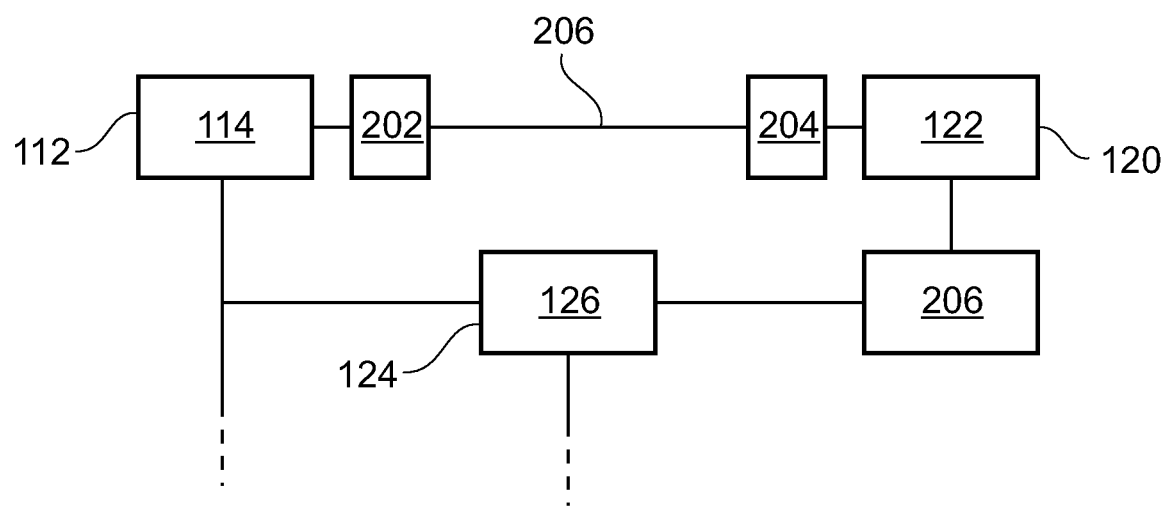

According to a further exemplary embodiment, schematically shown in FIG. 13, the pre-navigation data 114 comprises a phase reference signal 202 and the plurality of live images 122 each comprises a phase indicator 204. For the determination 124 of the spatial relation 126, from the plurality of the 2D images, only images 206 with a corresponding phase reference are selected. This is indicated by an arrow 206 between the phase reference signal box 202 and the phase indicator box 204. Thus, the pre-navigation data 114 and the selected images 206 are entering the spatial relation box 124, as indicated.

According to a further aspect, for the registration of the 2D image, image pixels with a first predetermined value are matched with image pixels or voxels with a predetermined second value.

According to a further aspect, the determining step 124 of the spatial relation 126 comprises temporal and spatial constraints.

For example, the temporal and spatial constraints are based upon previously performed spatial relation determinations, for example registrations.

According to a further aspect, a possible moving path of the element inside the vascular structure is determined.

Figure 14:
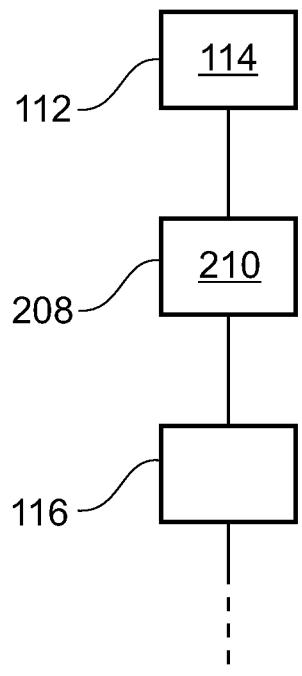

According to a further exemplary embodiment, before generating the vessel representation, the vascular structure with its vessel volumes is determined by a vessel segmentation 208 on the basis of the pre-navigation image data 114. For localizing the element, the live image data 122 is registered such that the element in the live image is positioned inside a vessel of the vascular structure (see FIG. 14).

Figure 15:
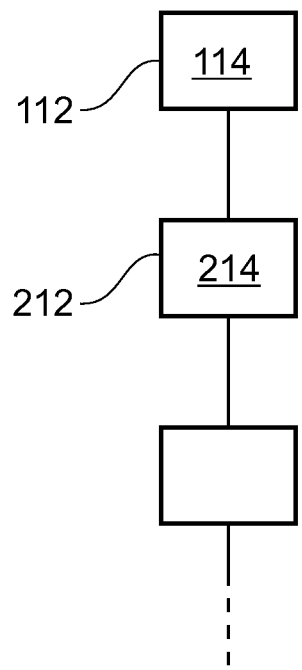

According to a further exemplary embodiment of the invention, shown in FIG. 15, the vascular structure with its vessel volumes is determined by generating 212 a model 214 on the basis of the pre-navigation image data 114 and the live image data 122 is registered such that an element in the live image data is positioned inside a vessel of the vascular structure.

According to a further aspect, the element is detected and a model of the element is generated and displayed overlaid to the 2D image such that the representation of the model of the element is visible in the tailored roadmap.

According to a further aspect, the non-selected vascular structure is attenuated in relation to the distance to the element. In other words, the vessel structure is fading the more, the greater the distance of the vessel path to the element. For example, the distance can be a geodesic distance that relates to the connecting path inside the vessel tree structure.

According to a further aspect, the live image 122 comprises at least two elements and the at least two elements are located inside the vascular structure.

As an example, the pre-navigation image data 114 comprises a 3D vessel tree in a neuro after C-arm CT reconstruction. The navigation data 122 comprises 2D live fluoroscopic images during a neuro intervention. In the determining step 124, the pre-navigation data is registered with live image data. Since the 2D live image data comprises several images, in the analyzing step 128, an intervention tool or intervention tools are identified and continuously localized. The generating step 116 comprises generating a vessel representation from the pre-registered pre-navigation data. The determining step 132 comprises the step of pruning off vessels away from the intervention in the current action range. Then, an overlay of the projection of the pruned vessel representation onto the live images is generated in step g). The output displayed in step h) comprises live images with tailored vessel roadmap overlay.

Figure 16:
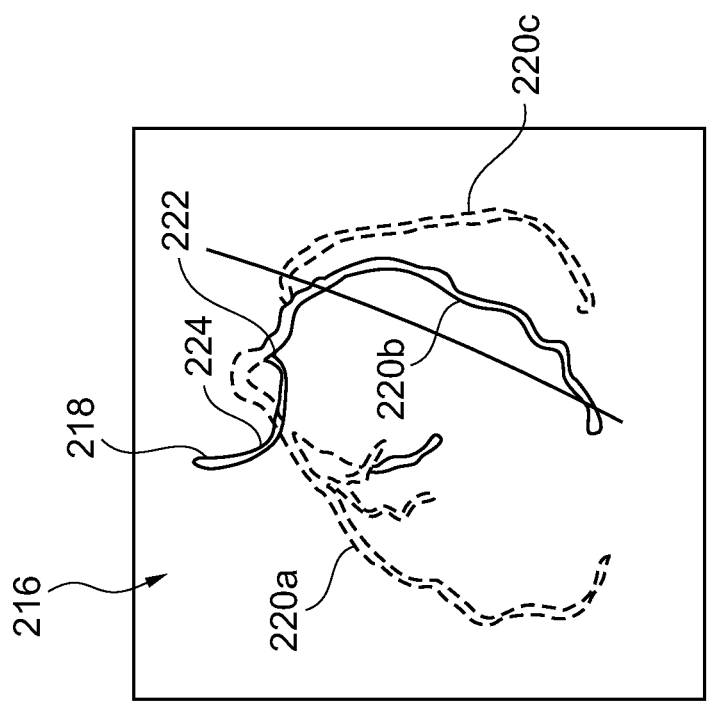
FIG. 16 schematically shows a customized vessel tree projection.

As a further example, FIG. 16 shows the result of step f), where a vessel representation 216 comprises tree-like vascular structure 218 with a plurality of sub-trees 220*a*, 220*b*, 220*c*, etc. As a result of the determination step 132, one of the sub-trees, in the example shown the sub-tree 220*b*, is determined in which an element 222 is positioned, wherein the determining is based on the localization of the element in step e) and on the spatial relation in step d). A portion of the vascular structure is selected based on the determined sub-tree, which portion in the example shown is the sub-tree 222*b* as well as the initial path of the main tree structure, indicated with reference number 224. The non-selected sub-trees, in the example shown the sub-trees 220*a* and 220*c*, are shown in attenuated manner with dotted lines to symbolize the step of pruning the vessel tree. For example, the pruned off branches 220*a* and 220*c* can be hidden completely or can be shown with dotted lines to give an indication for the other non-selected portions.

Figure 17:
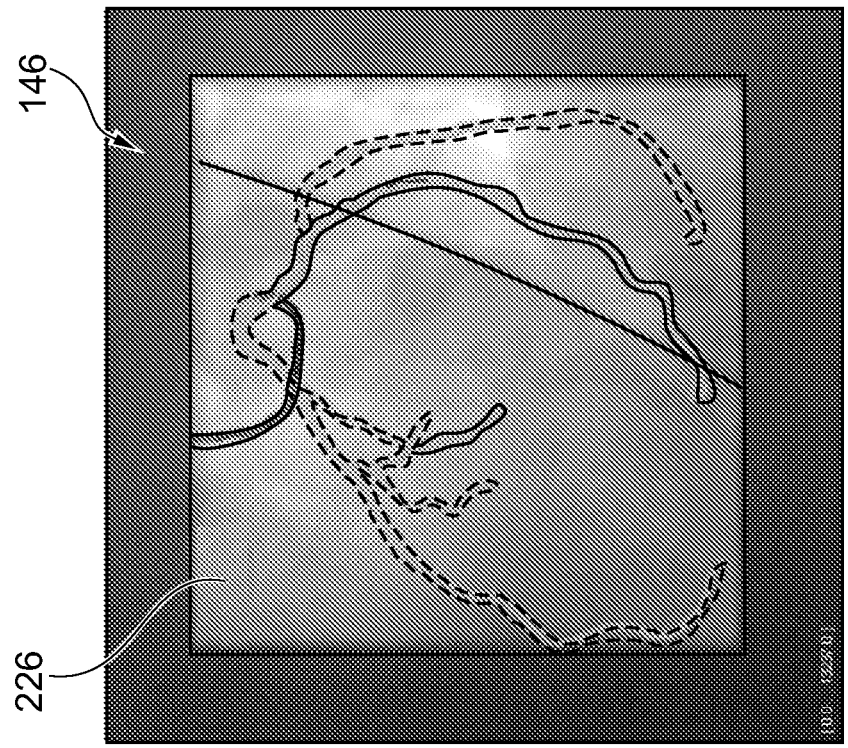
FIG. 17 schematically shows a tailored roadmap according to the invention.

FIG. 17 shows a combination of the manipulated tree-like structure of FIG. 16 and a fluoro image 226 as a life image data provided by acquisition step c) onto which the selected portion of the vascular structure, i.e. the vascular structure 216 of FIG. 16 is overlaid, too. Thus, the combination displayed in FIG. 17 represents the tailored roadmap 146 as described above.

Figure 18:
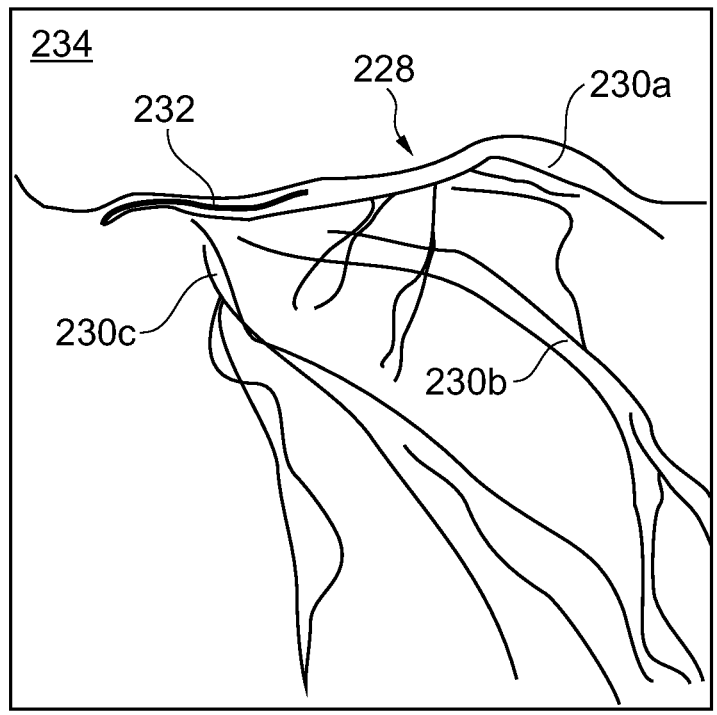
FIG. 18 schematically shows a non-adapted roadmap.

In FIG. 18, a vessel tree 228 is shown comprising several sub-trees 230, only a few of these are indicated with reference numerals 230*a*, 230*b*, and 230*c*. Further, an interventional device 232 as an element is also visible. The vessel tree projection 228 is overlaid to a fluoro image 234 acquired in acquisition step c). However, the roadmap shown is not further processed according to the invention, but rather shown as a comparison to FIG. 14, which shows a tailored roadmap according to the invention.

Figure 19:
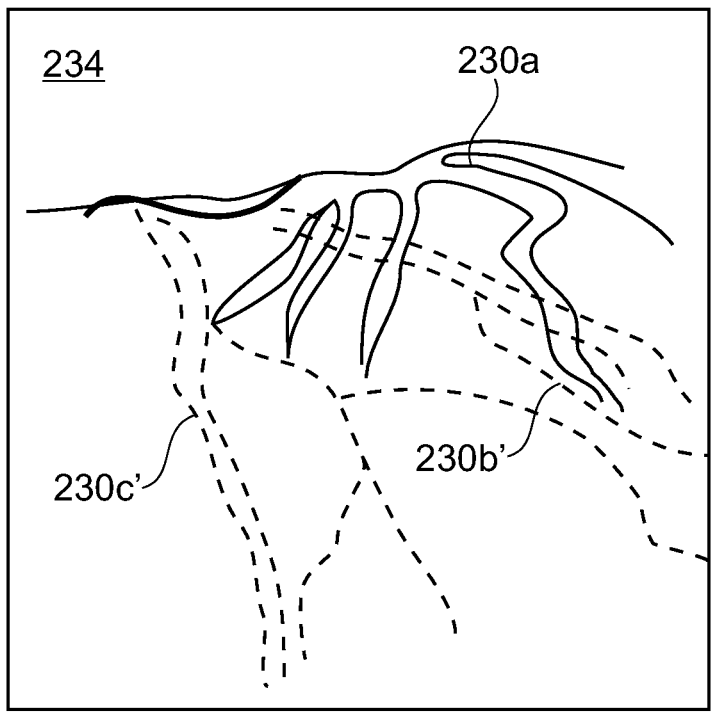
FIG. 19 shows the roadmap of FIG. 18 as a tailored roadmap according to the invention.

As can be seen from FIG. 19, those sub-trees 230*b*, 230*c* of the vessel tree 228 are non-selected portions of the vessel tree and are thus shown in an attenuated or pruned off manner, which is indicated by sub-trees 230*b'* and 230*c'* in dotted lines. Only the selected portion of the vessel tree, i.e. in the example shown the sub-tree 230*a*, is shown in combination with a fluoro live image 234 onto which the segmented vessel tree is overlaid. The result is a tailored roadmap which allows an easier and thus faster reception of the information to the user with respect to the present location of the device or element.

In another exemplary embodiment of the present invention (not shown), a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention (not shown), a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

The invention claimed is:

1. A device for adaptive roadmapping for examination of an object of interest, comprising:
   a processor configured to receive pre-navigation image data that represents at least a part of a vascular structure comprising a tree-like structure with a plurality of sub-trees, and to receive live image data of the object, wherein the object comprises the vascular structure, and wherein the vascular structure contains an element of interest; and
   a display;
   wherein the processor is further configured to generate a vessel representation based on the pre-navigation image data; to determine a spatial relation of the pre-navigation image data and live image data; to analyze the live image data by identifying and localizing the element in the live image data; to determine a sub-tree in which the element is positioned based on the localizing of the element and on the spatial relation, to select a portion of the vascular structure based on the determined sub-tree; and to generate a combination of the live image data and an image of the selected portion of the vascular structure; and
   wherein the display is adapted to display the combination as a tailored roadmap.

2. A medical imaging system for examination of an object of interest, comprising:
   a device for adaptive roadmapping; and
   an X-ray imager;
   wherein the X-ray imager is configured to acquire live image data of the object,
   wherein the device comprises a processor and a display, the processor being configured to
   receive pre-navigation image data that represents at least a part of a vascular structure comprising a tree-like structure with a plurality of sub-trees,
   receive live image data of the object, wherein the object comprises the vascular structure, and wherein the vascular structure contains an element of interest;
   wherein the processor is further configured to generate a vessel representation based on the ore-navigation image data; to determine a spatial relation of the pre-navigation image data and live image data; to analyze the live image data by identifying and localizing the element in the live image data; to determine a sub-tree in which the element is positioned based on the localizing of the element and on the spatial relation, to select a portion of the vascular structure based on the determined sub-tree; and to generate a combination of the live image data and an image of the selected portion of the vascular structure, and
   wherein the display is adapted to display the combination as a tailored roadmap.

3. A method for adaptive roadmapping for examination of an object of interest, the method comprising the acts of:
   providing pre-navigation image data that represents at least a part of a vascular structure comprising a tree-like structure with a plurality of sub-trees;
   generating a vessel representation based on the pre-navigation image data;
   acquiring live image data of the object, wherein the object comprises the vascular structure, and wherein the vascular structure contains an element of interest;
   determining spatial relation of the pre-navigation image data and the live image data;
   analyzing the live image data by identifying and localizing the element in the live image data;
   determining a sub-tree in which the element is positioned, wherein the determining act is based on the localizing of the element and on the spatial relation;
   selecting a portion of the vascular structure based on the determined sub-tree;
   generating a combination of the live image data and an image of the selected portion of the vascular structure; and
   displaying the combination as a tailored roadmap.

4. The method according to claim 3, further comprising the act of pruning off non-selected branch portions, wherein the displaying act displays the vascular structure with the selected portion only.

5. The method according to claim 3, further comprising the act of attenuating non-selected portions of the vascular structure in relation to a distance to the element, wherein the distance relates to a connecting path inside the vascular structure.

6. The method according to claim 3, further comprising the act of determining a plurality of sub-trees and branches of the vascular structure, wherein the selected portion of the vascular structure is visualized in the image for the combination in the displaying act.

7. The method according to claim 3, wherein the analyzing act is repeated for generating temporal information in case the act of determining the sub-tree in which the element is positioned leads to a predetermined degree of ambiguity, and wherein the temporal information is applied for determining the sub-tree in the displaying act.

8. The method according to claim 3, wherein the element located inside the vascular structure is visible in the live image data, and wherein the method further comprises an act of registering the pre-navigation image data and the live image data based upon the element.

9. The method according to claim 3, further comprises an act of registering the pre-navigation image data and the live image data, wherein the pre-navigation data comprises a phase reference signal, wherein the plurality of live images each comprises a phase indicator, and wherein for the registering act, from the plurality of the 2D images only images with a corresponding phase reference are selected.

10. The method according to claim 3, wherein before the act of generating the vessel representation, the vascular structure with its vessel volumes is determined by vessel segmentation based on the basis of the pre-navigation image data, and wherein for the localizing of the element, the live image data is registered such that the element in the live image is positioned inside a vessel of the vascular structure.

11. The method according to claim 3, further comprising the act of determining the vascular structure with its vessel volumes by generating a model based on the pre-navigation image data, and wherein the live image data is registered such that an element in the live image data is positioned inside a vessel of the vascular structure.

12. A non-transitory computer readable medium comprising computer instructions which, when executed by a processor, configure the processor to perform adaptive roadmapping for examination of an object of interest by performing the acts of:
  providing pre-navigation image data that represents at least a part of a vascular structure comprising a tree-like structure with a plurality of sub-trees;
  generating a vessel representation based on the pre-navigation image data;
  acquiring live image data of the object, wherein the object comprises the vascular structure, and wherein the vascular structure contains an element of interest;
  determining spatial relation of the pre-navigation image data and the live image data;
  analyzing the live image data by identifying and localizing the element in the live image data;
  determining a sub-tree in which the element is positioned, wherein the determining act is based on the localizing of the element and on the spatial relation;
  selecting a portion of the vascular structure based on the determined sub-tree;
  generating a combination of the live image data and an image of the selected portion of the vascular structure; and
  displaying the combination as a tailored roadmap.

* * * * *